United States Patent
Lawless et al.

(10) Patent No.: US 8,313,308 B2
(45) Date of Patent: Nov. 20, 2012

(54) MEDICAL INFUSION PUMP WITH CLOSED LOOP STROKE FEEDBACK SYSTEM AND METHOD

(75) Inventors: Michael W. Lawless, Ramona, CA (US); Marwan A. Fathallah, Mundelein, IL (US); Mansour A. Saleki, San Jose, CA (US); Brian A. Kidd, San Francisco, CA (US); Kent D. Abrahamson, Morgan Hill, CA (US); Robert P. Cousineau, San Jose, CA (US); Robert R. Boyd, Jacksonville, FL (US); Howard L. Greene, Worthington, OH (US)

(73) Assignee: Hospira, Inc., Lake Forest, IL (US)

( * ) Notice: Subject to any disclaimer, the term of this patent is extended or adjusted under 35 U.S.C. 154(b) by 539 days.

(21) Appl. No.: 10/810,123

(22) Filed: Mar. 26, 2004

(65) Prior Publication Data
US 2005/0214129 A1    Sep. 29, 2005

(51) Int. Cl.
*F04B 49/06*   (2006.01)
*F04B 43/12*   (2006.01)
(52) U.S. Cl. .................. 417/44.2; 417/44.1; 417/477.2
(58) Field of Classification Search ............ 417/44.1, 417/44.2, 118, 477.2, 20; 604/153
See application file for complete search history.

(56) References Cited

U.S. PATENT DOCUMENTS

| | | | |
|---|---|---|---|
| 3,985,467 A | 10/1976 | Lefferson | |
| 4,078,562 A | 3/1978 | Friedman | |
| 4,308,866 A | 1/1982 | Jelliffe et al. | |
| 4,411,651 A | 10/1983 | Schulman | |
| 4,453,931 A | 6/1984 | Pastrone | |
| 4,617,014 A | 10/1986 | Cannon et al. | |
| 4,696,671 A | 9/1987 | Epstein et al. | |
| 4,741,736 A | 5/1988 | Brown | |
| 4,846,792 A | 7/1989 | Bobo et al. | |
| 4,850,805 A * | 7/1989 | Madsen et al. | 417/18 |
| 4,886,422 A | 12/1989 | Takeuchi et al. | |
| 4,898,576 A | 2/1990 | Philip | |
| 4,919,595 A * | 4/1990 | Likuski et al. | 417/18 |
| 4,927,411 A | 5/1990 | Pastrone et al. | |
| 5,006,050 A | 4/1991 | Cooke et al. | |

(Continued)

FOREIGN PATENT DOCUMENTS
EP    0 282 323    3/1988

(Continued)

OTHER PUBLICATIONS

European Patent Office; Jun. 14, 2010; Search Report, Communication Pursuant to Article 94(3) EPC.

(Continued)

*Primary Examiner* — Devon C Kramer
*Assistant Examiner* — Philip Stimpert
(74) *Attorney, Agent, or Firm* — Michael R. Crabb

(57) ABSTRACT

A medical pump with a closed loop stroke feedback system and method, for use with a pumping chamber, for example in a cassette, is disclosed. The pump includes a pumping element that intermittently pressurizes a pumping chamber during a pumping cycle. A pressure sensor detects the pressure exerted by the pumping element on the pumping chamber. A position sensor detects the position of the pumping element. A processing unit processes pressure data from the pressure sensor and position data from the position sensor to determine a calculated stroke volume of the pump for a pump cycle, and to adjust a stroke frequency of the pump to compensate for variation in the stroke volume.

37 Claims, 10 Drawing Sheets

U.S. PATENT DOCUMENTS

| | | |
|---|---|---|
| 5,116,312 A | 5/1992 | Blakenship et al. |
| 5,174,472 A | 12/1992 | Raque et al. |
| 5,292,306 A | 3/1994 | Wynkoop et al. |
| 5,399,171 A | 3/1995 | Bowman et al. |
| 5,464,392 A * | 11/1995 | Epstein et al. .............. 604/67 |
| 5,482,438 A | 1/1996 | Anderson et al. |
| 5,551,850 A | 9/1996 | Williamson et al. |
| 5,554,013 A | 9/1996 | Owens et al. |
| 5,586,868 A * | 12/1996 | Lawless et al. ................ 417/53 |
| 5,658,133 A | 8/1997 | Anderson et al. |
| 5,938,636 A | 8/1999 | Kramer et al. |
| 5,957,890 A | 9/1999 | Mann et al. |
| 6,259,587 B1 | 7/2001 | Sheldon et al. |
| 6,267,559 B1 | 7/2001 | Mossman et al. |
| 6,497,680 B1 | 12/2002 | Holst et al. |
| 7,104,763 B2 | 9/2006 | Bouton et al. |
| 7,360,999 B2 * | 4/2008 | Nelson et al. ................ 417/63 |
| 2001/0007636 A1 * | 7/2001 | Butterfield ................ 417/477.1 |
| 2002/0013545 A1 | 1/2002 | Soltanpour et al. |
| 2002/0018720 A1 | 2/2002 | Carlisle et al. |
| 2002/0168278 A1 * | 11/2002 | Jeon et al. ................ 417/559 |
| 2002/0183693 A1 | 12/2002 | Peterson et al. |
| 2003/0055375 A1 * | 3/2003 | Holst et al. ................ 604/67 |
| 2003/0091442 A1 | 5/2003 | Bush et al. |
| 2004/0047736 A1 | 3/2004 | Nose et al. |
| 2004/0120825 A1 | 6/2004 | Bouton et al. |
| 2004/0247445 A1 * | 12/2004 | Nelson et al. ................ 417/1 |
| 2005/0021297 A1 | 1/2005 | Hartlaub |
| 2005/0143864 A1 | 6/2005 | Blomquist |
| 2005/0187515 A1 | 8/2005 | Varrichio et al. |
| 2005/0214129 A1 | 9/2005 | Greene et al. |
| 2005/0235732 A1 | 10/2005 | Rush |
| 2005/0235733 A1 | 10/2005 | Holst et al. |

FOREIGN PATENT DOCUMENTS

| | | |
|---|---|---|
| EP | 0 291 727 | 4/1988 |
| EP | 02/82323 | 9/1988 |
| EP | 0291727 | 11/1988 |
| EP | 0960627 | 5/1999 |
| EP | 0960627 | 12/1999 |
| WO | 91/00113 | 1/1991 |
| WO | 98/04304 | 2/1998 |
| WO | 99/52575 | 10/1999 |
| WO | 00/13726 | 3/2000 |
| WO | 02/087664 | 11/2002 |
| WO | 02087664 | 11/2002 |
| WO | 2004/035115 | 4/2004 |
| WO | 2004/112579 | 12/2004 |
| WO | 2006/022906 | 3/2006 |

OTHER PUBLICATIONS

K. R. Dunster, et al., Flow Continuity of Infusion Systems at Low Flow Rates, Anaesthesia and Intensive Care, Oct. 1995, vol. 23, No. 5, pp. 605-609, Oct. 1995.

S. Crystal Coley, et al., Performance of three portable infusion-pump devices set to deliver 2 mL/hr, Amer. J. of Health System Pharmacy, Jun. 1997, vol. 54, pp. 1277-1280.

Ilfeld, et al., Delivery Rate Accuracy of Portable, Bolus-Capable Infusion Pumps Used to Patient-Controlled Continuous Regional Analgesia, Regional Anesthesia and Pain Medicine, Jan.-Feb. 2003, vol. 28, No. 1, pp. 17-23.

Ilfeld, et al., Portable Infusion Pumps Used for Continuous Regional Analgesia: Delivery Rate Accuracy and Consistency, Regional Anesthesia and Pain Medicine, Sep.-Oct. 2003, vol. 28, No. 5, pp. 424-432.

* cited by examiner

MEDICAL INFUSION PUMP WITH CLOSED LOOP STROKE FEEDBACK SYSTEM AND METHOD

BACKGROUND OF THE INVENTION

The present invention relates to a means of determining and controlling the operating condition of a medical pump. More particularly, this invention relates to a means of adjusting a stroke frequency of a pump to compensate for individual variation in the stroke volume delivered by the medical pump.

Modern medical care often involves the use of medical pump devices to deliver fluids and/or fluid medicine to patients. Medical pumps permit the controlled delivery of fluids to a patient, and such pumps have largely replaced gravity flow systems, primarily due to the pump's much greater accuracy in delivery rates and dosages, and due to the possibility for flexible yet controlled delivery schedules. Of the modern medical pumps, those incorporating a diaphragm are often preferred because they provide a more accurate controlled rate and volume than do other types of pumps.

A typical positive displacement pump system includes a pump device driver and a disposable fluid or pumping chamber, defined in various forms including but not limited to a cassette, syringe barrel or section of tubing. A disposable cassette, which is adapted to be used only for a single patient and for one fluid delivery cycle, is typically a small plastic unit having an inlet and an outlet respectively connected through flexible tubing to the fluid supply container and to the patient receiving the fluid. The cassette includes a pumping chamber, with the flow of fluid through the chamber being controlled by a plunger or pumping element activated in a controlled manner by the device driver.

For example, the cassette chamber may have one wall formed by a flexible diaphragm that is reciprocated by the plunger and the driver to cause fluid to flow. The pump driver device includes the plunger or pumping element for controlling the flow of fluid into and out of the pumping chamber in the cassette, and it also includes control mechanisms to assure that the fluid is delivered to the patient at a pre-set rate, in a pre-determined manner, and only for a particular pre-selected time or total dosage.

The fluid enters the cassette through an inlet and is forced through an outlet under pressure. The fluid is delivered to the outlet when the pump plunger forces the membrane into the pumping chamber to displace the fluid. During the intake stroke the pump plunger draws back, the membrane covering the pumping chamber pulls back from its prior fully displaced configuration, and the fluid is then drawn through the open inlet and into the pumping chamber. In a pumping stroke, the pump plunger forces the membrane back into the pumping chamber to force the fluid contained therein through the outlet. Thus, the fluid flows from the cassette in a series of spaced-apart pulses rather than in a continuous flow.

One of the requirements for a medical pump is that it is able to deliver precise volumes at precise delivery rates. Conventional pumps, in general, rely on nominal or empirical data to estimate the delivery volumes and delivery rates, and do not provide mechanisms for adjusting an actual delivery due to variations from this nominal or empirical data. This lack of adjustment during an actual delivery limits the accuracy of these pumps.

It is therefore a principal object of this invention to provide means for adjusting a stroke frequency of the pump to compensate for variation in the stroke volume based on pressure data from the medical pump.

These and other objects will be apparent to those skilled in the art.

SUMMARY OF THE INVENTION

A medical pump with a closed loop stroke feedback system and method, for use with a fluid chamber or pumping chamber, is disclosed. The fluid or pumping chamber can be included in or defined by a cassette, syringe barrel, or section of tubing. The pump includes a pumping element that intermittently pressurizes the pumping chamber during a pumping cycle. A pressure sensor detects the pressure exerted by the pumping element on the pumping chamber. A position sensor detects the position of the pumping element. A processing unit processes pressure data from the pressure sensor and position data from the position sensor to determine a calculated stroke volume of the pump for a pump cycle, and to adjust a stroke frequency of the pump to compensate for variation in the stroke volume.

In operation, the processing unit sets a stroke frequency for a desired dosage rate based on a nominal stroke volume, determines when an outlet valve of the pumping chamber opens, determines a calculated pressurization volume from a beginning of the pump cycle to the point when the outlet valve opens, determines a change in pressurization volume by subtracting the calculated pressurization volume from a nominal pressurization volume, determines a change in stroke volume by multiplying the change in pressurization volume by a ratio of pumping chamber expansion under pressure at the middle of the pumping cycle to pumping chamber expansion under pressure at the start of the pumping cycle, determines a calculated stroke volume based on the change in stroke volume, and adjusts the stroke frequency to compensate for variation between the calculated stroke volume and the nominal stroke volume.

DETAILED DESCRIPTION OF THE PREFERRED EMBODIMENT

Figure 1:
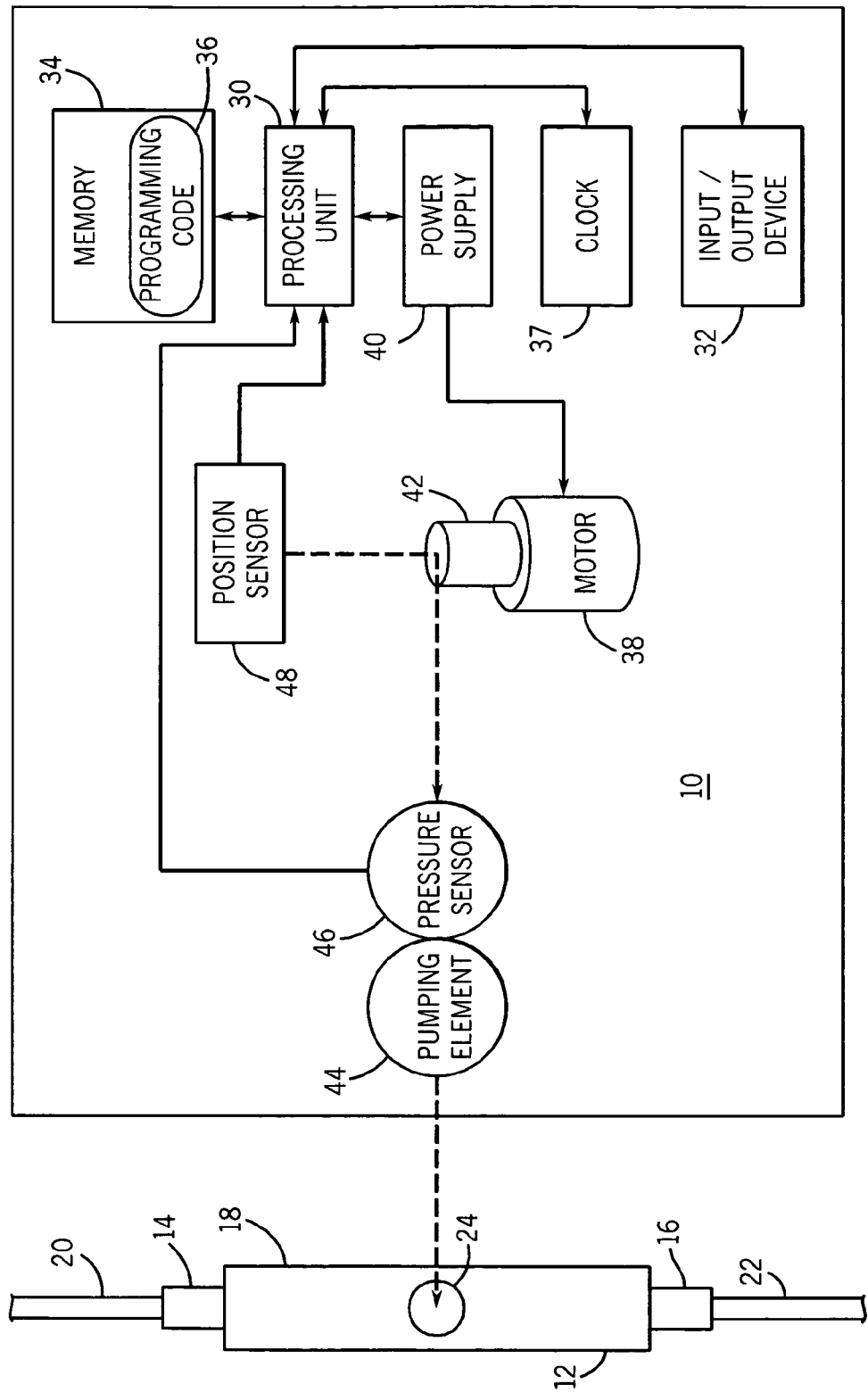
FIG. 1 is a schematic diagram of one embodiment of a medical pump according to the present invention.

With reference to FIG. 1, the functional components of one embodiment of a medical pump 10 are shown in schematic form. The medical pump 10 is used in connection with a disposable fluid chamber, such as a cassette 12 for delivering a fluid to a patient. As will be described below in greater detail the medical pump 10 of the present invention provides a mechanism for adjusting an actual delivery of fluid based on variations from nominal data used to estimate pump performance. It will be understood to one of ordinary skill in the art that the term medical pump as used herein includes but is not limited to enteral pumps, infusion pumps, cassette pumps, syringe pumps, peristaltic pumps, or any positive displacement fluid pumping device for the delivery of fluids intravenously or intra-arterially to a patient.

The medical pump 10 and cassette 12 are shown with several components for implementing the present invention. Those of ordinary skill in the art will appreciate that the pump 10 and cassette 12 may include many more components than those shown in FIG. 1. However, it is not necessary that all these components be shown in order to disclose an illustrative embodiment for practicing the present invention.

Figure 5:
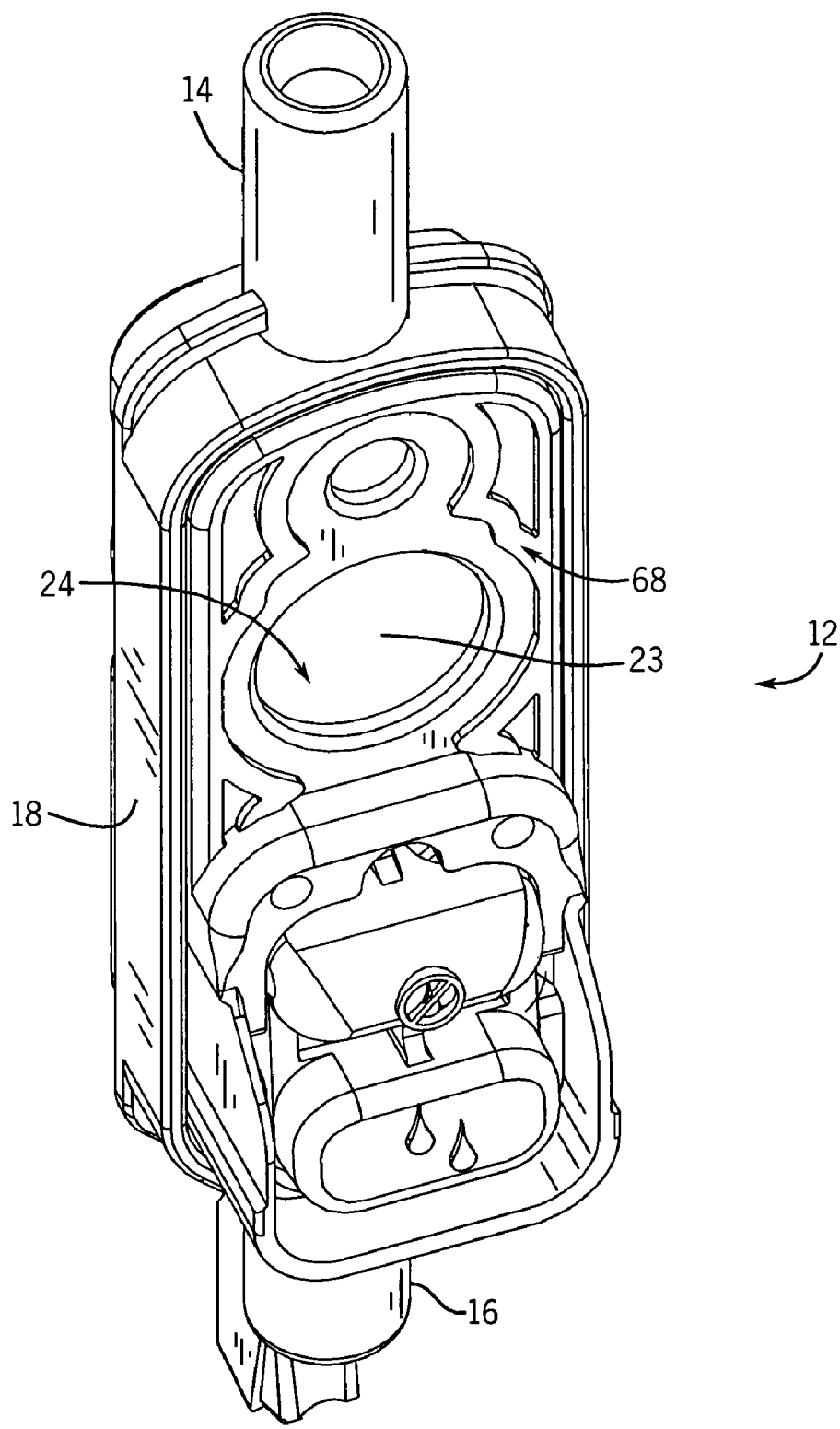
FIG. 5 is a perspective view of a cassette, which can be used as the pumping chamber in accordance with one embodiment of the present invention.

With reference to FIG. 5, one cassette 12 suitable for use with the present invention is shown. It will be understood to one of ordinary skill in the art that a cassette or fluid chamber having a different design than that shown in FIG. 5 may be used with pump 10 without departing from the present invention.

The cassette 12 may include an inlet 14 and an outlet 16 formed in main body 18. An inlet fluid line 20 couples the inlet port 14 on the main body 18 to a fluid source (not shown) such as an IV bag or other fluid container. Similarly, an outlet fluid line 22 couples the outlet port 16 on main body 18 to the body of a patient (not shown).

Figure 6:
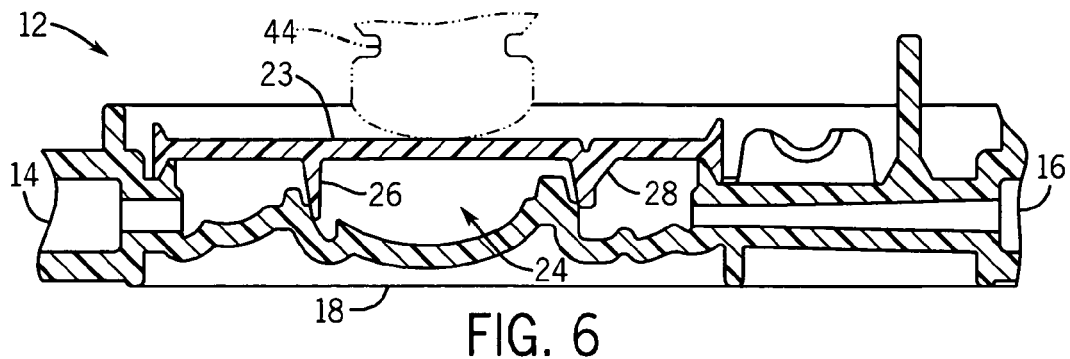
FIGS. 6-9 are cross sectional views of the pumping element of the present invention driving a cassette through a pumping cycle.

With reference to FIG. 6, a resilient elastomeric membrane or diaphragm 23 forms a pumping chamber 24, inlet valve 26, and outlet valve 28 on an inner face 68 of the main body 18. The pumping chamber 24 is connected in fluid flow communication between the inlet port 14 and the outlet port 16. The pumping chamber 24 operates to meter fluid through the cassette 12.

The inlet valve 26 resides between inlet port 14 and the pumping chamber 24. Inlet valve 26 operates to physically open and close the fluid communication between inlet port 14 and pumping chamber 24.

Similarly, the outlet valve 28 resides between the pumping chamber 24 and outlet port 16. Outlet valve 28 operates to physically open and close the fluid communication between pumping chamber 24 and outlet port 16. The pumping chamber 24, inlet valve 26, and outlet valve 28 are all operatively associated with the pump 10 to control the flow of fluid through the cassette 12. As will be understood from the description below, the cassette is a passive valve system requiring pressurization of the pumping chamber 24 prior to fluid delivery. Inlet valve 26 and outlet valve 28 react to the pressure of the pumping element 44 on the pumping chamber 24.

Figure 7:
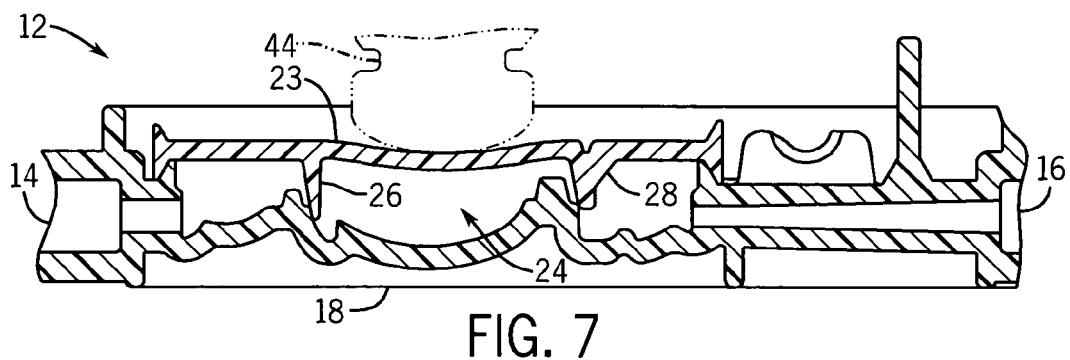
Figure 8:
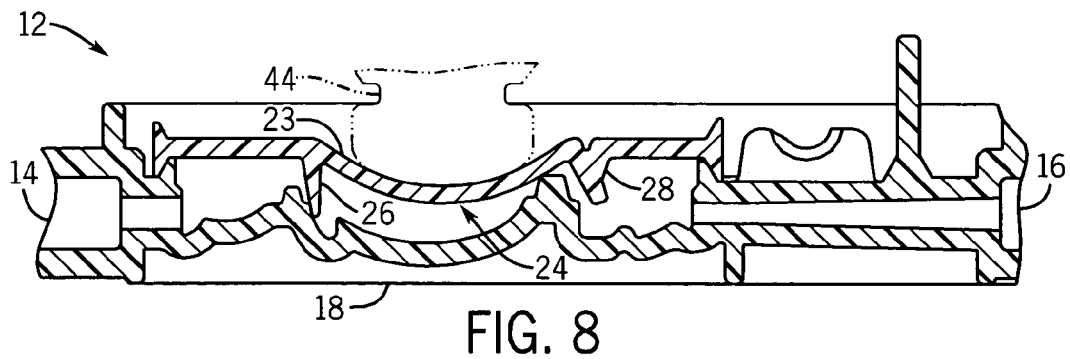
Figure 9:
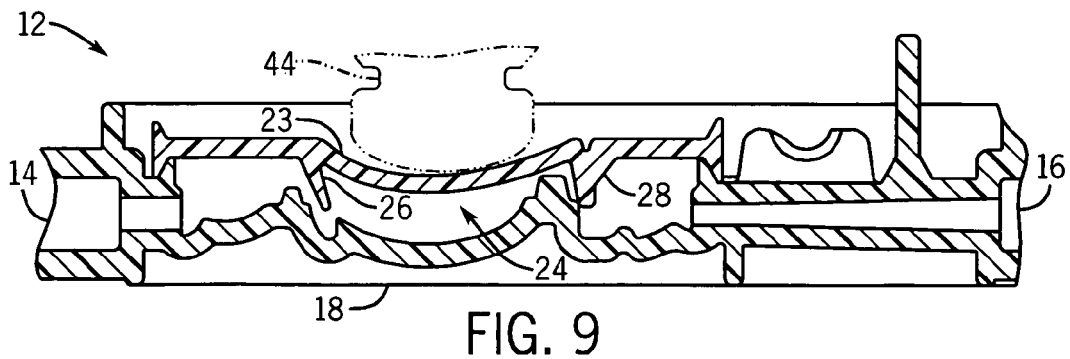

In operation, fluid enters through the inlet 14 and is forced through outlet 16 under pressure. The fluid is delivered to the outlet 16 when the pump 10 displaces the membrane 23 and thereby compresses the pumping chamber 24 to expel the fluid. As shown in FIG. 6, the pumping cycle begins with the pumping chamber 24 in a non-compressed position. As shown in FIG. 7, as the pump 10 begins to displace the membrane 23 on the pumping chamber 24, the pumping chamber 24 is compressed while the outlet valve 28 remains closed. As shown in FIG. 8, once the pump 10 displaces the membrane 23 on the pumping chamber 24 to a given extent, the outlet valve 28 opens and fluid flows to the outlet 16. As shown in FIG. 9, during the intake stroke the pump 10 releases the resilient membrane 23 over the pumping chamber 24, and the fluid is then drawn through the inlet 14 and into the pumping chamber 24 once inlet valve 26 opens. Thus, the fluid flows from the cassette 12 in a series of spaced-apart pulses rather than in a continuous flow. The fluid is delivered to the patient at a pre-set rate, in a pre-determined manner, and only for a particular pre-selected time or total dosage.

Referring to FIG. 1, a processing unit 30 is included in pump 10 and performs various operations described in greater detail below. An input/output device 32 communicates with the processing unit 30 and allows the user to receive output from processing unit 30 and/or input information or commands into the processing unit 30. Those of ordinary skill in the art will appreciate that input/output device 32 may be provided as a separate display device and a separate input device.

A memory 34 communicates with the processing unit 30 and stores code and data necessary for the processing unit 30 to calculate and output the operating conditions of pump 10. More specifically, the memory 34 stores a programming code 36 formed in accordance with the present invention for processing data to determine and control the operating condition of the pump 10.

A clock 37 is used to keep time in the pump 10. The clock 37 is connected to the processing unit 30, and provides the processing unit 30 with time information for correlating data over time or conducting time sensitive activities.

An electric motor 38 is controlled by processing unit 30 and is energized by a power supply 40 to serve as a prime mover for rotatably driving a shaft 42 connected to the motor 38. The processing unit 30 orders the motor 38 to run at different speeds depending on the flow rate desired through the pump 10. The down-stroke or delivery portion of the stroke has the motor 38 running directly from power supply 40. The up-stroke, retract or fill portion of the stroke is run at a voltage set by the processing unit 30, so that the retract times are varied by the processing unit 30, where higher desired flow rates require faster retract speeds.

A pumping element 44 is operatively associated with the shaft 42. When energized, the pumping element 44 reciprocates back and forth to periodically down-stroke, causing pumping element 44 to press on pumping chamber 24, and expel fluid therefrom. On an up-stroke, pumping element 44 releases pressure from pumping chamber 24 and thereby draws fluid from inlet port 16 into pumping chamber 24. Thus, the pumping element 44 intermittently pressurizes the pumping chamber 24 during a pumping cycle.

A pressure sensor 46 is operatively associated with the pumping element 44 to detect the force or pressure exerted by the pumping element 44 on the pumping chamber 24. As shown, the pressure sensor 46 is directly connected to the pumping element and is positioned in-line with the pumping element 44, between the pumping chamber 24 and the shaft 42. The pressure sensor 46 is the only pressure sensor included in the medical pump 10, and operates to sense the force on pumping element 44 as well as to generate a pressure signal based on this force. The pressure sensor 46 is in electronic communication with the processing unit 30 to send the pressure signal to the processing unit 30 for use in determining operating conditions of pump 10. One of ordinary skill in the art will appreciate that the pressure sensor 46 may be a force transducer or any other device that can operatively sense the pressure brought to bear on the pumping chamber 24 by pumping element 44.

A position sensor 48 is operatively associated with the pumping element 44 to directly or indirectly detect the position of the pumping element 44. The position sensor 48 tracks the pumping cycle of pump 10 by detecting the position of the pumping element 44. As shown, the position sensor 48 is associated with the shaft 42. The position sensor 48 generates a position signal by detecting the rotational position of the shaft 42. The position sensor 48 is in electronic communication with the processing unit 30 to send the position signal to the processing unit 30. The processing unit 30 utilizes this information to associate the incoming pressure data with a particular portion of the pump cycle. One of ordinary skill in the art will appreciate that the position sensor 48 could alternatively track a cam attached to the shaft 42 or the pumping element 44. Additionally, one of ordinary skill in the art will appreciate that the position sensor 48 as used herein includes but is not limited to mechanical indicators such as pivoting dial indicators, electronic switches, Hall Effect sensors, and optical based position detectors.

Figure 2:
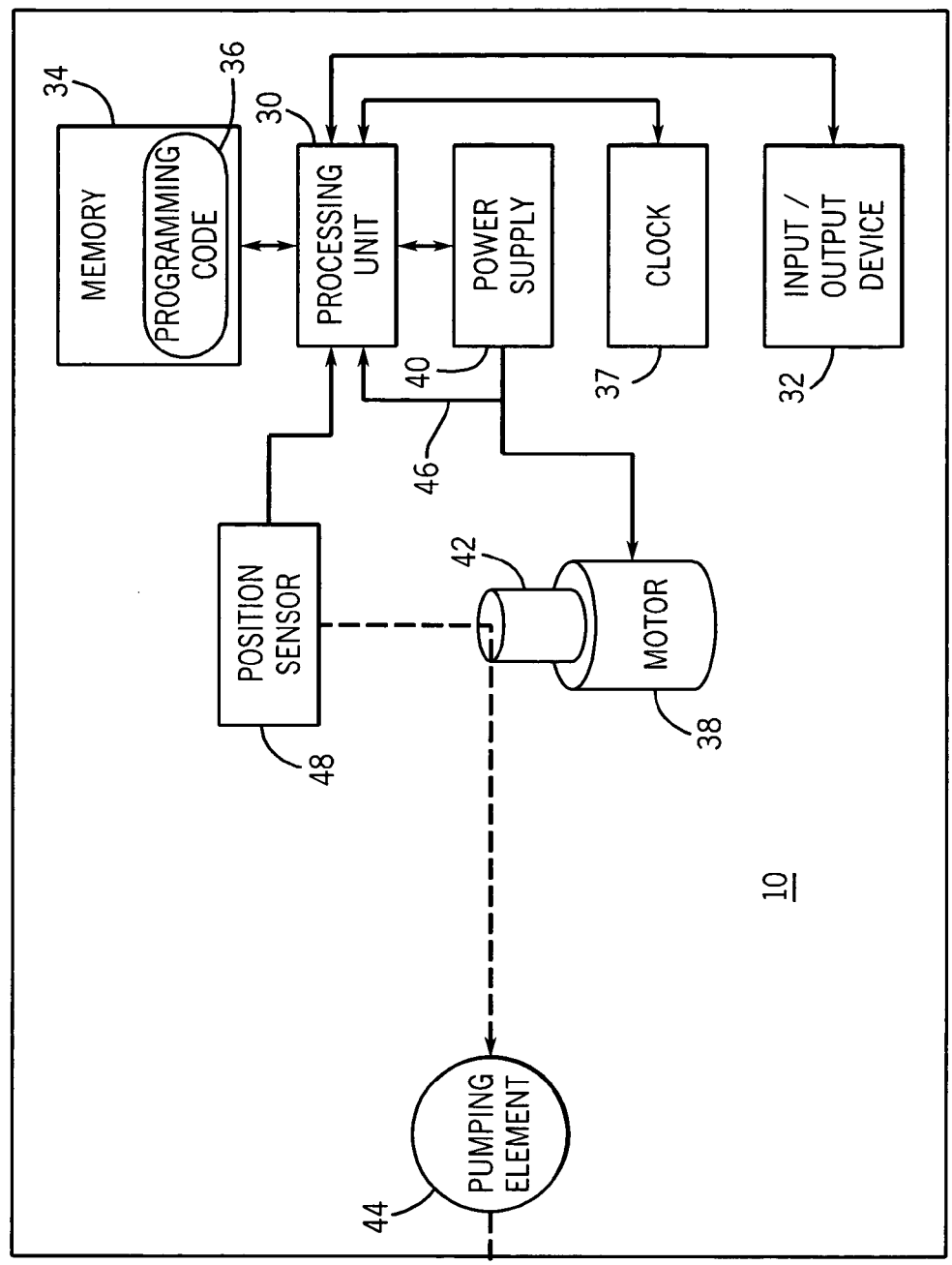
FIG. 2 is schematic diagram of an alternative embodiment of a medical pump according to the present invention.

Referring to FIG. 2, an alternative embodiment of the medical pump 10 is shown. In this embodiment the pressure sensor 46 comprises a current signal from the motor 38. The current signal from the motor 38 is proportional to the force exerted on the pumping chamber 24 through the pumping element 44 by the motor 38. As is also the case in FIG. 1, the pressure sensor 46 is the only pressure sensor included in the medical pump 10, and operates to sense the force on pumping element 44 as well as to generate a pressure signal to the processing unit 30 based on this force.

Figure 3:
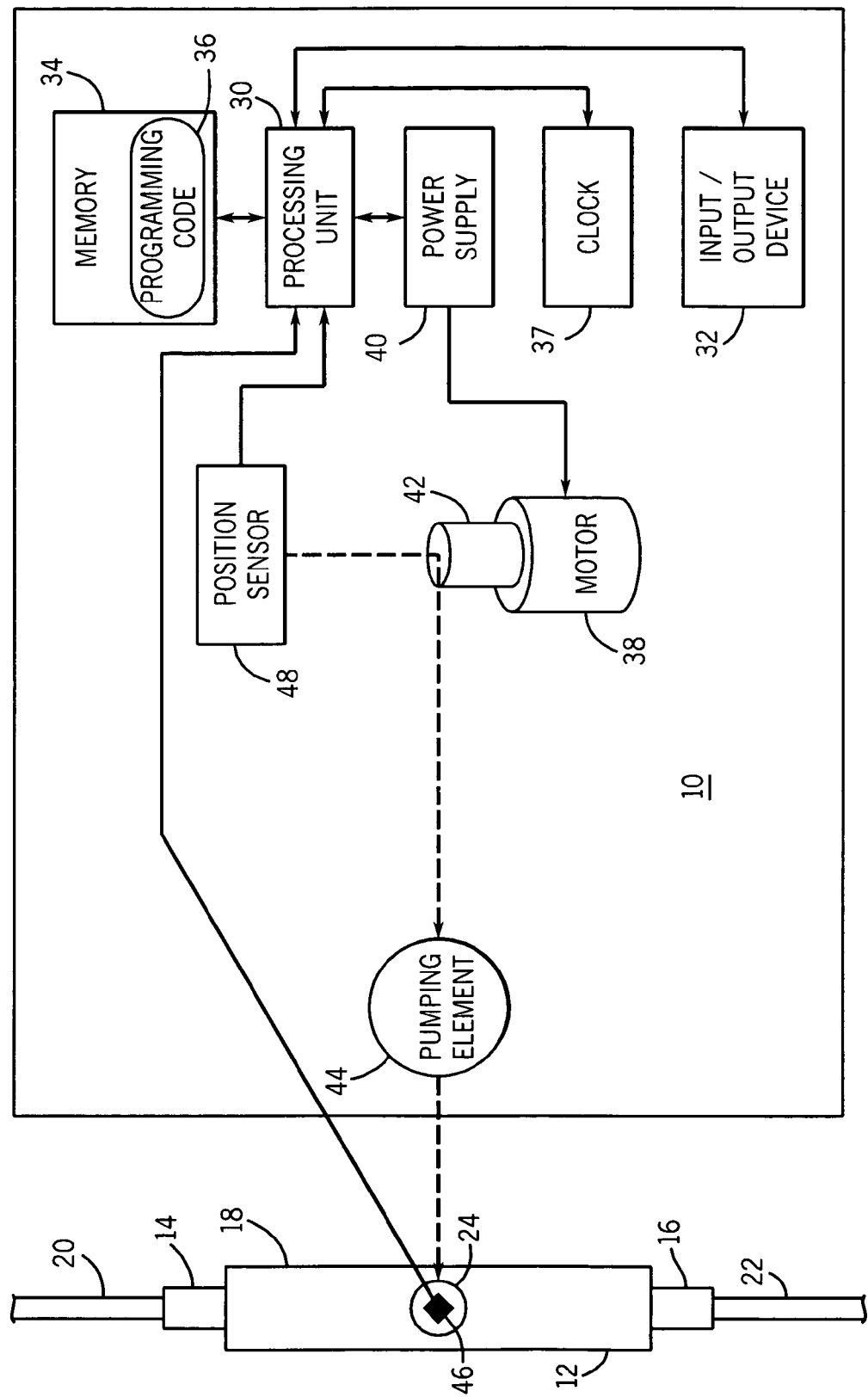
FIG. 3 is schematic diagram of another alternative embodiment of a medical pump according to the present invention.

Referring to FIG. 3, another alternative embodiment of the medical pump 10 is shown. In this embodiment the pressure sensor 46 comprises a strain gauge directly connected to the pumping chamber 24 of the cassette 12. The current signal from the strain gauge is proportional to the force exerted on the pumping chamber 24 by the pumping element 44. As is also the case in FIG. 1, the pressure sensor 46 is the only pressure sensor included in the medical pump 10, and operates to sense the force on pumping element 44 as well as to generate a pressure signal to the processing unit 30 based on this force.

Figure 4:
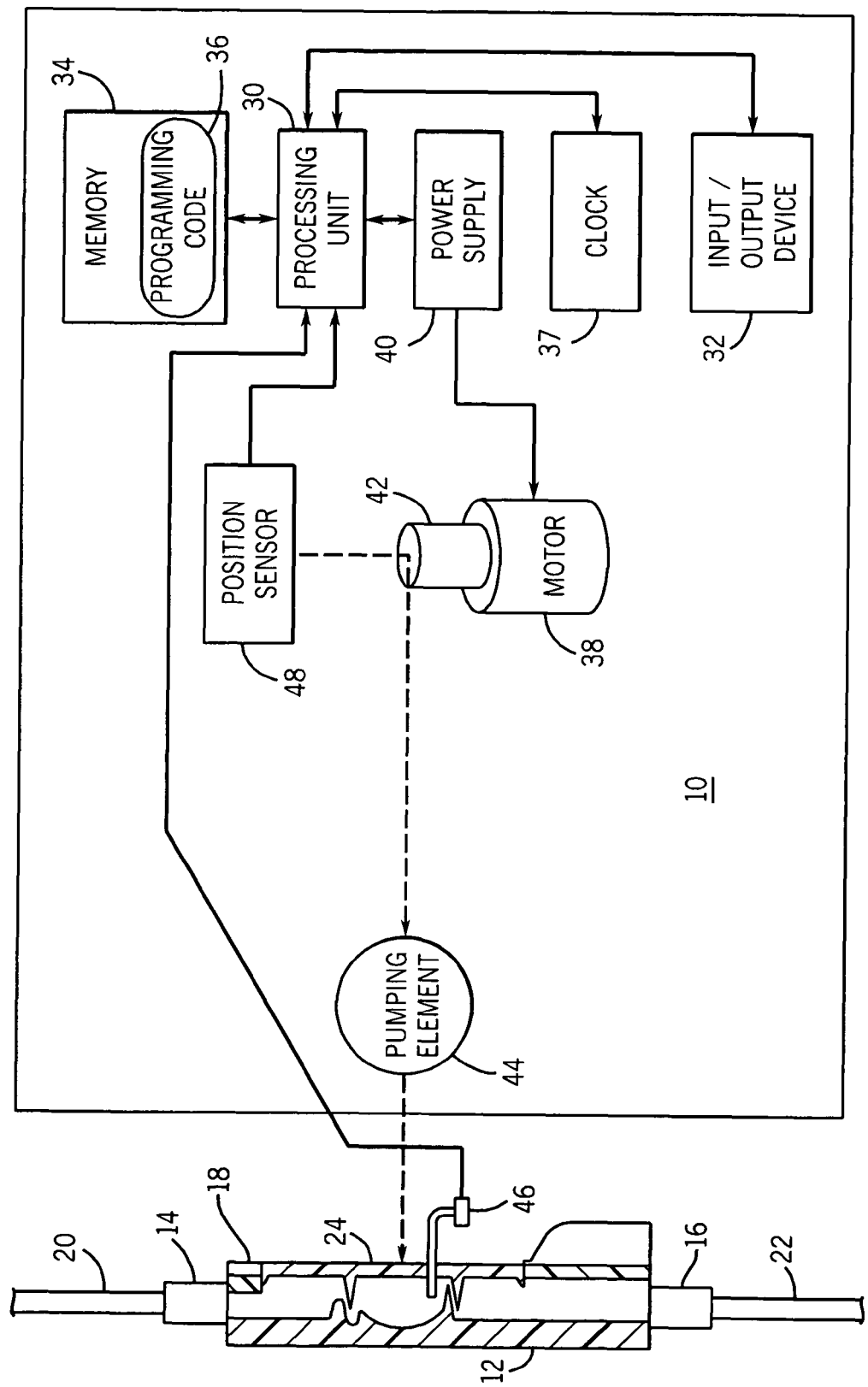
FIG. 4 is schematic diagram of another alternative embodiment of a medical pump according to the present invention.

Referring to FIG. 4, yet another alternative embodiment of the medical pump 10 is shown. In this embodiment the pressure sensor 46 comprises a pressure probe located at least partially within the pumping chamber 24 of the cassette 12. The current signal from pressure probe is proportional to the force exerted on the pumping chamber 24 by the pumping element 44. As is also the case in FIG. 1, the pressure sensor 46 is the only pressure sensor included in the medical pump 10, and operates to sense the force on pumping element 44 as well as to generate a pressure signal to the processing unit 30 based on this force.

Figure 10:
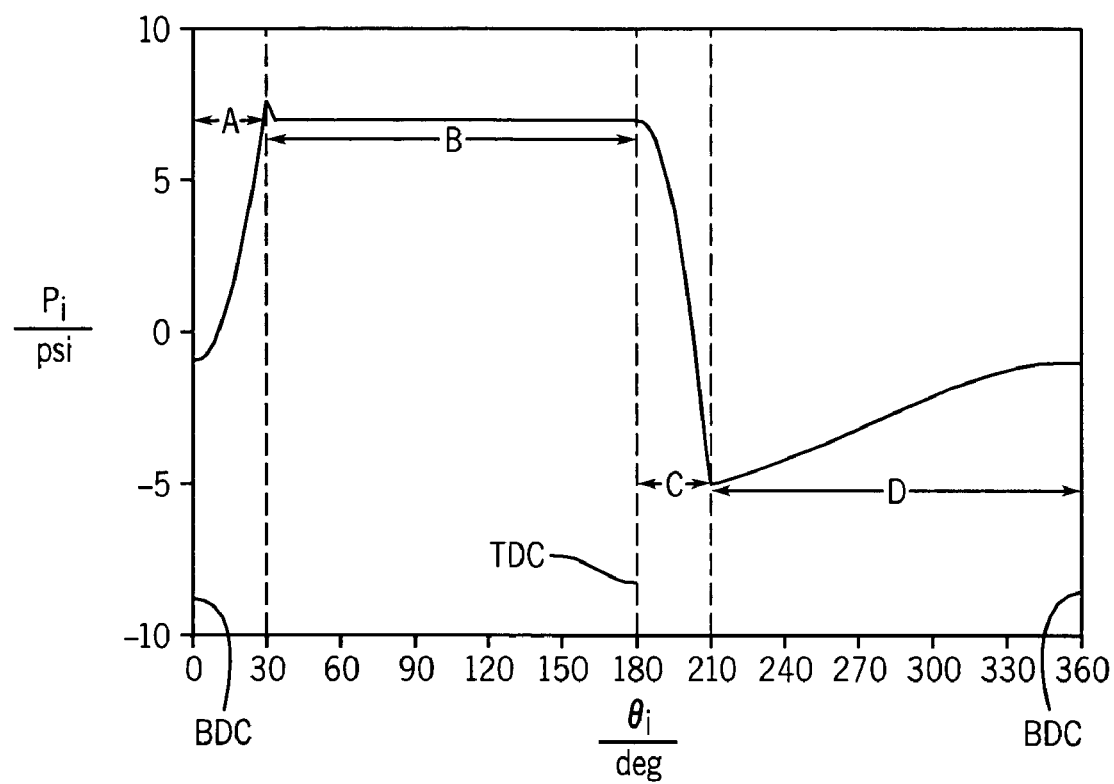
FIG. 10 is a graph plotting force data versus the pump plunger position from a pump cycle.

Referring to FIG. 10, an exemplary force curve is shown where the pumping element 44 applies force pi (shown in psi units) to the pumping chamber 24 while moving in essentially a constant cyclic (sine-wave) motion through 360 degrees $\theta_i$ (shown in units of degrees) of rotation per cycle. The pumping element 44 always has sufficient force available from the motor 38 so that its speed is essentially independent of the force $p_i$ applied to the pumping element 44, and the outlet flow from pumping chamber 24 is not restricted.

The curve starts at 0 degrees or Bottom Dead Center (BDC) with the pumping element 44 deflecting the diaphragm 23 of the pumping chamber 24 a minimal amount at this point. The position of the pumping element 44 at 0 degrees, and the resultant displacement of pumping chamber 24 can be seen in FIG. 6.

Cycle portion A shows the pressurization of the pumping chamber 24 and is shown in this example as occurring from 0 to 30 degrees. During the pressurization cycle portion A, the pumping element 44 moves into the cassette 12 (which is called the pressurization stroke because fluid is compressed in pumping chamber 24 of the cassette 12) building force within the pumping chamber 24, while the outlet valve 28 remains closed. The position of the pumping element 44 between 0 and 30 degrees, and the resultant displacement of pumping chamber 24 can be seen in FIG. 7.

A delivery cycle portion B begins when the force within the pumping chamber 24 is sufficient to open the outlet valve 28. During the delivery cycle portion B, the pumping element 44 moves into the cassette 12 so as to build a force within the pumping chamber 24 sufficient to open the outlet valve 28 and expel fluids from the pumping chamber 24. The delivery cycle portion B is shown in this example as occurring from 30 to 180 degrees. The position of the pumping element 44 between 30 and 180 degrees, and the resultant opening of the outlet valve 28 can be seen in FIG. 8.

The delivery cycle portion B ends at Top Dead Center (TDC), or 180 degrees of rotation, and a depressurization cycle portion C begins. The depressurization cycle portion C shows the depressurization the pumping chamber 24 and is shown in this example as occurring from 180 to 210 degrees. During the depressurization cycle portion C, the pumping element 44 moves out of the cassette 12 (which is called the up-stroke, depressurization or inlet stroke) and the force drops off. As the diaphragm 23 returns to its initial position, while the inlet valve 26 remains closed, negative pressure builds within the pumping chamber 24.

A refill cycle portion D begins when the negative pressure within the pumping chamber 24 is sufficient to the open the inlet valve 26. During the refill cycle portion D, the pumping element 44 moves out the cassette 12 building negative pressure within the pumping chamber 24 sufficient to open the inlet valve 26 and draw fluids into the pumping chamber 24. The refill cycle portion D is shown in this example as occurring from 210 to 360 degrees, or Bottom Dead Center (BDC). The position of the pumping element 44 between 210 to 360 degrees, and the resultant opening of the inlet valve 26 can be seen in FIG. 9.

Figure 11:
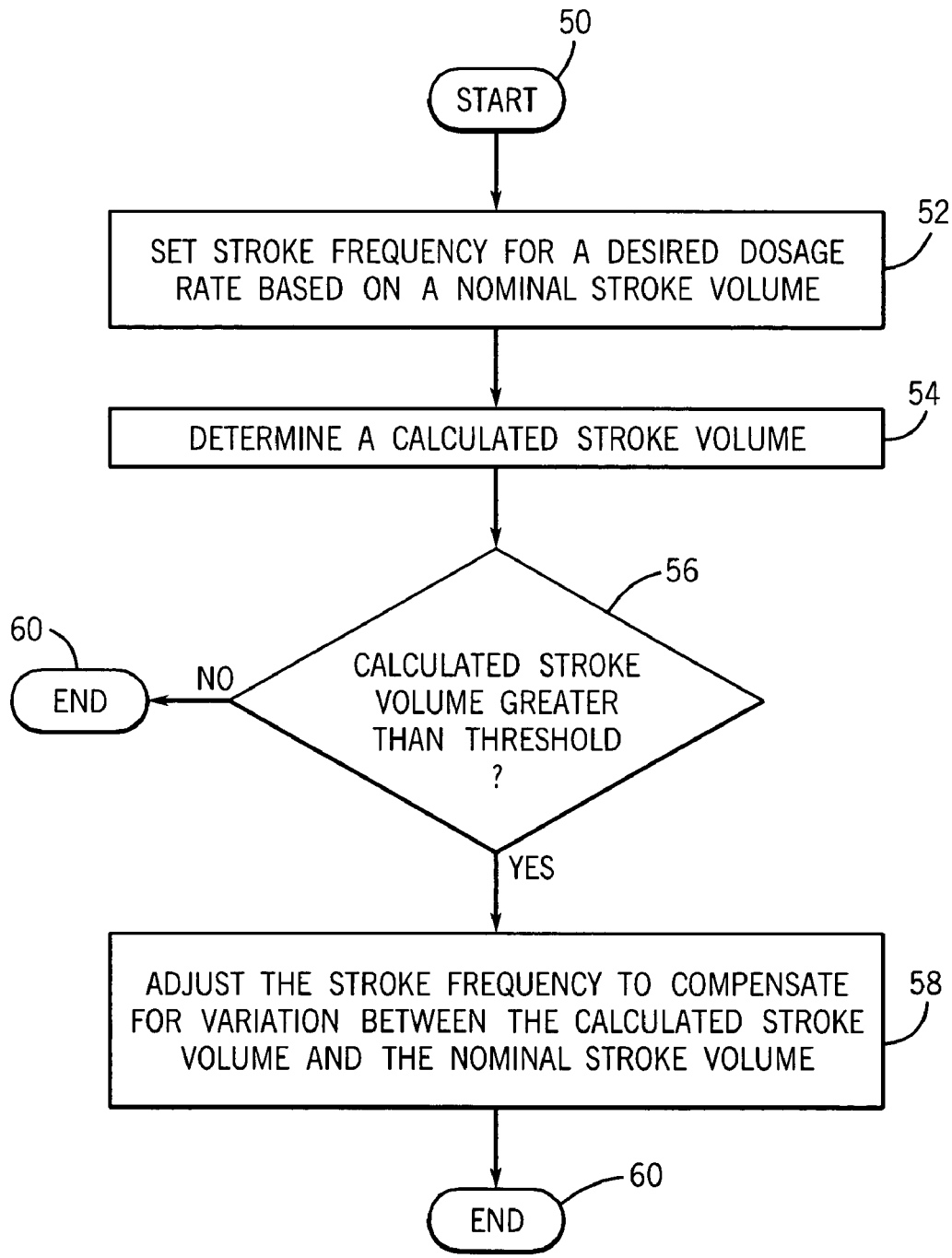
FIG. 11 is a flow chart illustrating one embodiment of determining and adjusting the operating condition of a medical pump according to the present invention.

Referring to FIGS. 1 and 11, the pump 10 of the present invention provides a mechanism for controlling or adjusting an actual delivery of fluid based on variations from nominal data used to estimate pump performance. The processing unit 30 retrieves the operating condition programming code 36 from memory 34 and applies it to the pressure and position data received during this pump cycle. The pump pressure data and pump position data are processed by the processing unit 30. Sensing the force that the resilient diaphragm 23 of the pumping chamber 24 exerts against the pumping element 44 and analyzing that force can determine an estimated volume of fluid flow per stroke (calculated stroke volume). The processing unit 30 utilizes the calculated stroke volume in a closed loop stroke feedback system to modify the stroke frequency to compensate for variation in the stroke volume. In the closed loop stroke feedback system, the processing unit 30 adjusts an actual delivery of fluid based on variation between the calculated stroke volume and nominal data used to estimate pump performance.

Specifically, the processing unit 30 begins execution of the programming code 36 at a block 50 and proceeds to block 52 where the processing unit 30 sets a stroke frequency for a desired dosage rate. The stroke frequency is determined by the processing unit 30 based on a nominal stroke volume. This nominal stroke volume can be supplied from empirical evidence of an average normal stroke volume for all pumps of a particular type or for each individual pump. Once the stroke frequency is set, the processing unit 30 proceeds to block 54 where it determines a calculated stroke volume of the pump for a pump cycle based on the pressure data from the pressure sensor 46 and position data from the position sensor 48. Once the calculated stroke volume has been determined, the processing unit 30 proceeds to decision block 56 where it determines if the calculated stroke volume is greater than a given threshold value. One of ordinary skill in the art will understand that the threshold value disclosed herein is predetermined from experimental data, and will vary from pump model to pump model.

If the result from decision block 56 is negative, then the execution of the programming code 36 by the processing unit 30 is complete and ends in block 60. If the result from decision block 56 is positive, then the processing unit 30 proceeds to block 58 where it adjusts the stroke frequency to compensate for the variation between the calculated stroke volume and the nominal stroke volume. Once the stroke frequency has been adjusted, the execution of the programming code 36 by the processing unit 30 is complete and ends in block 60.

Figure 12:
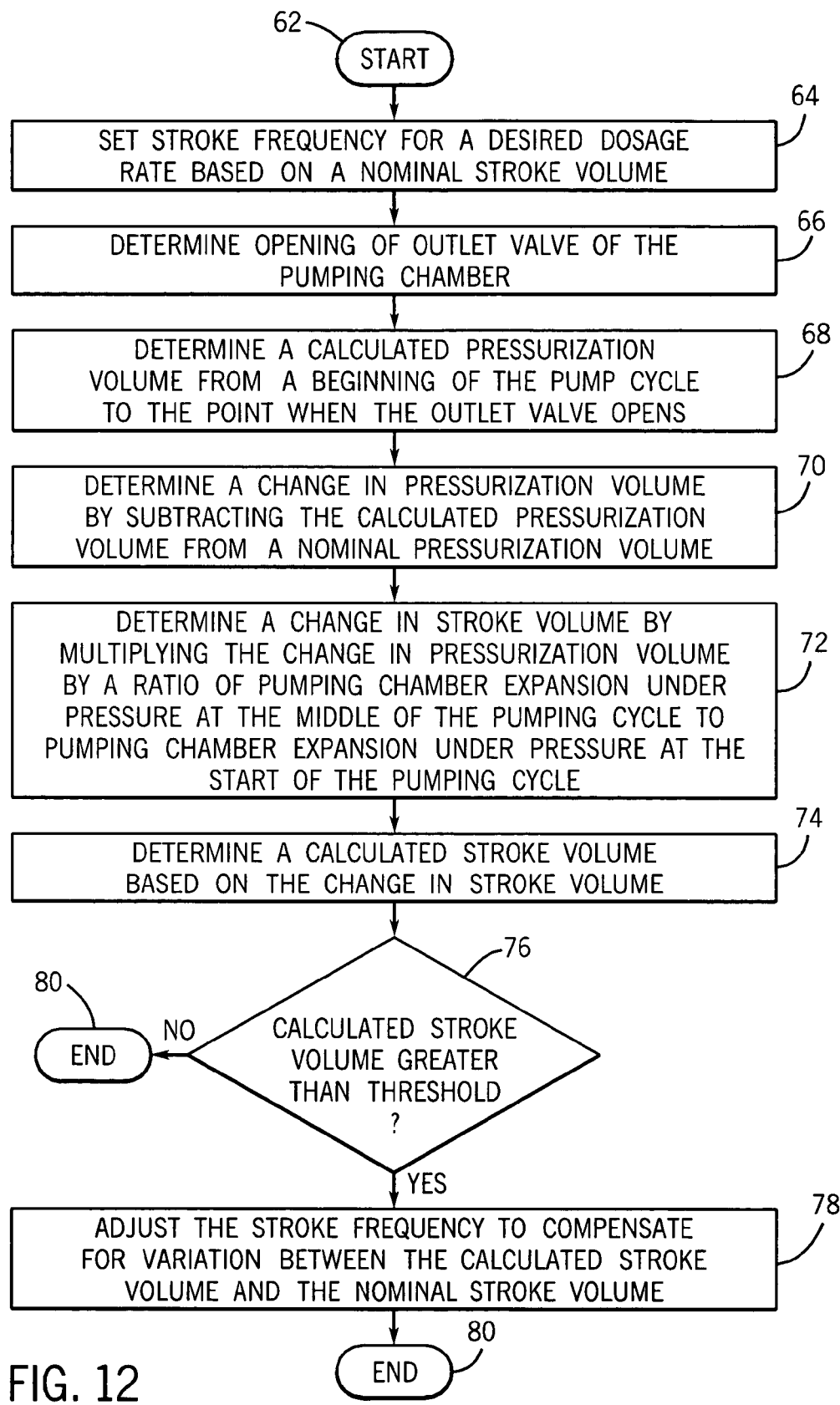
FIG. 12 is a flow chart illustrating a further embodiment of determining and adjusting the operating condition of a medical pump according to the present invention.

Referring to FIGS. 1, 10 and 12, a further embodiment of determining the operating condition of a medical pump according to the present invention is shown. Like the embodiment shown in FIG. 11, in the present embodiment, the processing unit 30 retrieves the operating condition programming code 36 from memory 34 and applies it to the pressure and position data received during this pump cycle. The pump pressure data and pump position data are processed by the processing unit 30. Sensing the force that the diaphragm 23 of the pumping chamber 24 exerts against the pumping element 44 and analyzing that force can determine an estimated volume of fluid flow per stroke (calculated stroke volume). The processing unit 30 utilizes the calculated stroke volume in a closed loop stroke feedback system to modify the stroke frequency to compensate for variation in the stroke volume. In the closed loop stroke feedback system, the processing unit 30 adjusts an actual delivery of fluid based on variation between the calculated stroke volume and nominal data used to estimate pump performance.

Specifically, the processing unit 30 begins execution of the programming code 36 at a block 62 and proceeds to block 64 where the processing unit 30 sets a stroke frequency for a desired dosage rate. Like step 52 from FIG. 10, the stroke frequency is determined by the processing unit 30 based on a nominal stroke volume.

Once the stroke frequency is set, the processing unit 30 proceeds to block 66 where the processing unit 30 determines when an outlet valve 28 of the pumping chamber opens. The processing unit 30 determines the opening of outlet valve 28 based on data from the pressurization cycle portion A (as shown in FIG. 10). During the pressurization cycle portion A pumping element 44 moves into the cassette 12 building force within the pumping chamber 24 to a point where the outlet valve 28 opens.

Specifically, by monitoring the slope of the pressure data over time, the opening of the outlet valve 28 can be determined. For instance, by taking the derivative of the pressure data over time, where the pressure derivate is greater than zero in the following equation:

$$\frac{dp}{dt} > 0$$

the pressure within the pumping chamber 24 is increasing and the outlet valve 28 remains closed. Where the pressure derivate is less than zero in the following equation:

$$\frac{dp}{dt} < 0$$

the pressure within the pumping chamber 24 is decreasing and the outlet valve 28 has opened, and the processing unit 30 determines at what angular position the pumping element 44 was in when the outlet valve 28 opened (i.e., where dp/dt changes from >0 to <0).

Once the outlet valve 28 opening is determined, the processing unit 30 proceeds to block 68 where the processing unit 30 determines a calculated pressurization volume from the beginning of the pump cycle to the point when the outlet valve opens. The processing unit 30 determines the calculated pressurization volume based on data from the pressurization cycle portion A (as shown in FIG. 10). During the pressurization cycle portion A pumping element 44 moves into the cassette 12 building force within the pumping chamber 24, while the outlet valve 28 remains closed.

Specifically, the processing unit 30 converts the angle at which the outlet valve 28 opens to a displacement distance of the pumping element 44 as follows:

$$x_i = L_{cam} * (1 - \cos(\theta_i))$$

where $x_i$ is the displacement distance, $L_{cam}$ is half the distance of a stroke for the pumping element 44, and $\theta_i$ is the angular position of the pumping element 44 at which the outlet valve 28 opened. The processing unit 30 converts the displacement distance $x_i$ into a pressurization stroke volume based on a ratio of volume to displacement distance for the pump 10. This ratio is based on a nominal pressurization volume and a nominal displacement distance for a typical pump 10. This pressurization volume and a nominal displacement distance can be supplied from empirical evidence of an average normal stroke volume for all pumps of a particular type or for each individual pump.

Once the calculated pressurization volume is determined, the processing unit 30 proceeds to block 70 where the processing unit 30 determines a change in pressurization volume by subtracting the calculated pressurization volume from a nominal pressurization volume. Again, the nominal pressurization volume can be supplied from empirical evidence of an average normal stroke volume for all pumps of a particular type or for each individual pump.

The change in pressurization volume determined here is proportional to variations in the actual stroke volume, as a portion of compressive forces can be lost and not translated into fluid delivery. For instance, a portion of compressive forces can be lost where there is excessive compliance within mechanical components (such as the cassette 12) or air bubble entrained within the pumping chamber 24.

Once the change in pressurization volume is determined, the processing unit 30 proceeds to block 72 where the processing unit 30 determines a change in stroke volume by multiplying the change in pressurization volume by a ratio of pumping chamber expansion under pressure at the middle of the pumping cycle to pumping chamber expansion under pressure at the start of the pumping cycle. This "pumping chamber expansion under pressure" is also referred to as the compliance of the pumping chamber. For instance, the diaphragm 23 of the cassette 12 is constructed of various materials with corresponding spring rates. As pressure is placed on the pumping chamber 24, the volume of the chamber 24 changes according to the overall spring rate of the cassette 12. As the volume of the pumping chamber 24 will grow larger as pressure increases. However, the pumping chamber compliance is not the same throughout the pumping cycle. At the beginning of the pumping cycle (0 degrees) the compliance (ratio of volume change to pressure) is higher than the compliance at the middle of the pumping cycle (180 degrees). Again, the compliance can be supplied from empirical evidence of an average normal stroke volume for all pumps of a particular type or for each individual pump. Thus, to better estimate the change in stroke volume, the change in pressurization volume is multiplied by a ratio of compliance at the middle of the pumping cycle to the compliance at the beginning of the pumping cycle.

Once the change in stroke volume is determined, the processing unit 30 proceeds to block 74 where the processing unit 30 determines a calculated stroke volume based on the change in stroke volume. Specifically, the change in stroke volume is added to the nominal stroke volume to arrive at the calculated stroke volume. This calculated stroke volume provides a very close estimate of the actual individual stroke volume delivered.

Once the calculated stroke volume has been determined, the processing unit 30 proceeds to decision block 76 where it determines if the calculated stroke volume is greater than a given threshold value. One of ordinary skill in the art will understand that the threshold value disclosed herein is predetermined from experimental data, and will vary from pump model to pump model. If the result from decision block 76 is negative, then the execution of the programming code 36 by the processing unit 30 is complete and ends in block 80.

If the result from decision block 76 is positive, then the processing unit 30 proceeds to block 78 where it adjusts the stroke frequency to compensate for the variation between the calculated stroke volume and the nominal stroke volume. Once the stroke frequency has been adjusted, the execution of the programming code 36 by the processing unit 30 is complete and ends in block 80.

It will be understood that the threshold determination above from block 76, could be made on criterional information other than the calculated stroke volume above. For instance, the threshold determination 76 could similarly be made based on the angle at which the outlet valve 28 opens, the calculated pressure volume, the change in pressurization volume, or the change in stroke volume determined above. In any of these cases, the given threshold value would necessarily be scaled according to the designated alternative criterional information. Additionally, the timing of the threshold determination 76 could also be adjusted based on the designated alternative criterional information. For instance, were the calculated pressurization volume designated as the alternative criterional information, the threshold determination 76 could occur at any point after step 68.

Likewise, it will be understood that the stroke frequency adjustment above from block 78, could be made on criterional information other than the calculated stroke volume above. For instance, the stroke frequency adjustment 78 could similarly be made based on the angle at which the outlet valve 28 opens, the calculated pressure volume, the change in pressurization volume, or the change in stroke volume determined above. In any of these cases, the stroke frequency adjustment 78 would necessarily be scaled according to the designated alternative criterional information. Additionally, the timing of the stroke frequency adjustment 78 could also be adjusted based on the designated alternative criterional information. For instance, were the calculated pressurization volume designated as the alternative criterional information, the stroke frequency adjustment 78 could occur at any point after step 68.

Additionally, further restrictions can be placed on the execution of the stroke frequency adjustment 78 step. For example, the calculated stroke volume could comprise multiple calculated stroke volumes averaged together. This averaging of multiple calculated stroke volumes potentially reduces the effects that minor variations in stroke volume and/or statistical noise have to the overall pump 10 operation.

In operation, the above closed loop stroke feedback system embodiments provide several advantages. The first advantage is that the actual volume delivered per stroke can be used by the processing unit 30 to continuously adjust the stroke rate. The second advantage is that the detection of the pressure data profile and the determination of the opening of outlet valve 28 permits the processing unit 30 to determine lost stroke volume (i.e. calculated stroke volume as compared with the nominal stroke volume) and to use this as an indicator of presence of air in the pumping chamber 24, as well as determining the size of air bubbles in the set. These advantages of the present invention limit the effects of all causes of delivery error, including: compliance of physical components, air in the delivery fluid, variations in line pressure, and manufacturing variability of physical components (for example, in valve opening pressures).

In cassette type pumps the present invention is particularly advantageous. As the cassettes are disposable, the cassettes are produced in very high volumes there are limitations to reducing the manufacturing variability of the physical components and assemblies. The overall accuracy provided by present invention improves the ability to perform accurate deliveries within a broader range of these manufacturing variabilities of the physical components and assemblies.

The third advantage is that the detection of the pressure data profile and the determination of the opening of outlet valve 28 permits the processing unit 30 to deliver in smaller increments for very low flow rates in a more continuous manner (known as Low Flow Continuity). In general, Low Flow Continuity is defined as the ability of a pump to deliver at rates of 1 ml/hr to 0.1 ml/hr or less with periods of "no-flow" not exceeding 20 seconds and bolus volumes not exceeding 2 micro-liters. To meet the highest Emergency Care Research Institute (ECRI) industry standards for Low Flow Continuity and achieve an "Excellent" ECRI rating, the pump must deliver fluid in increments no greater than two micro-liters at a flow rate of 0.1 milliliter per hour with a maximum "no-flow" period of 20 seconds.

Figure 13:
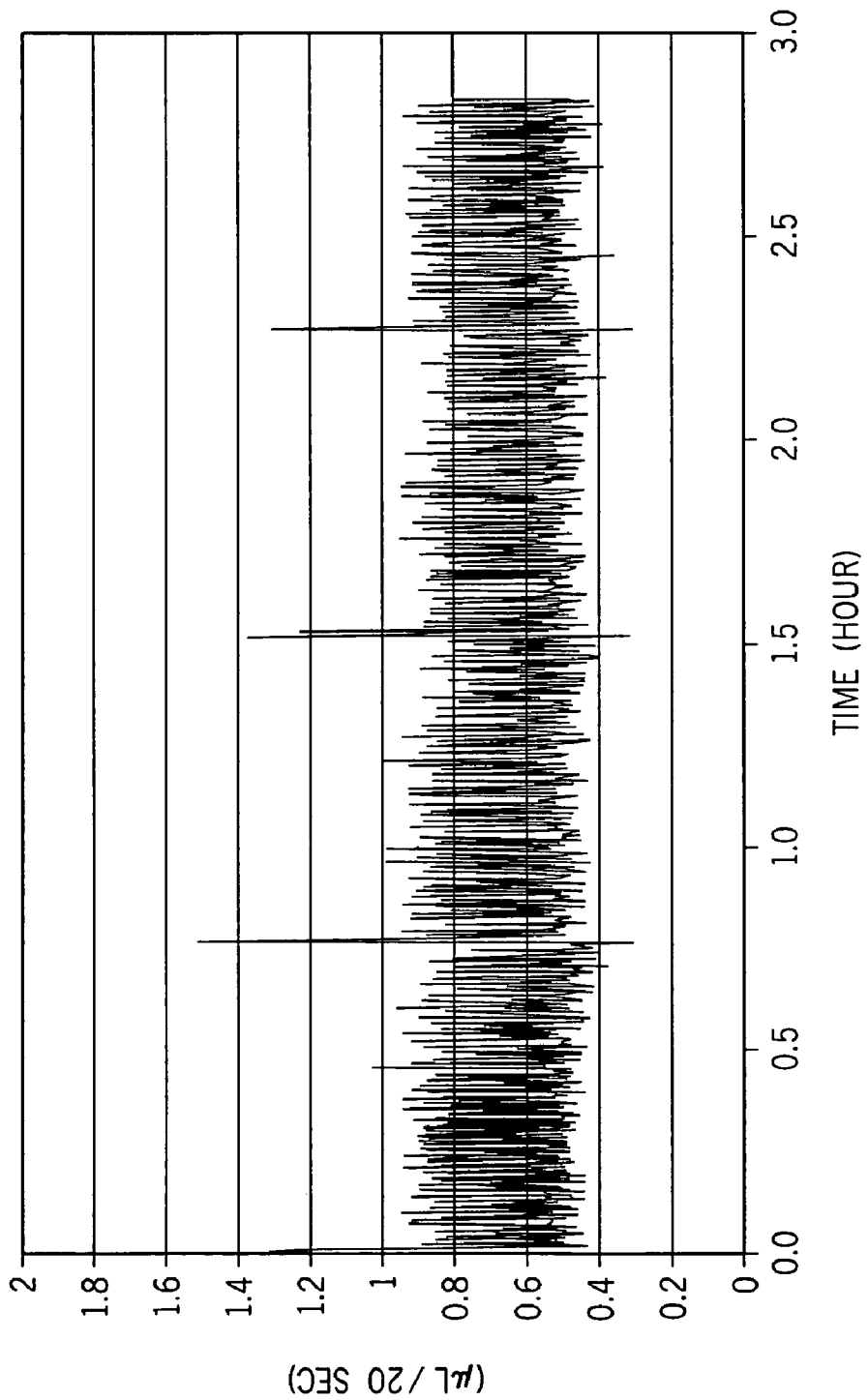
FIG. 13 is a graph of twenty second incremental bolus volume versus time using the present invention.

As shown in FIG. 13, the present invention provides means for reciprocating a plunger mechanism 44 of a medical pump 10 to deliver fluid in smaller increments for very low flow rates in a more continuous manner sufficient to meet and exceed the above ECRI standards. Specifically, FIG. 13 displays a pump delivering fluid with a low flow continuity of about 1 ml/hr or less, more specifically about 0.1 ml/hr or less, with twenty second incremental bolus volumes of less than 2 μl using the present invention. Advantageously, the same pump is also programmable to deliver up to 1000 ml/hr.

Whereas the invention has been shown and described in connection with the embodiments thereof, it will be understood that many modifications, substitutions, and additions may be made which are within the intended broad scope of the following claims. From the foregoing, it can be seen that the present invention accomplishes at least all of the stated objectives.

What is claimed is:

1. A medical pump for use with a pumping chamber, comprising:
 a plunger, disposed between a passive inlet valve and a passive outlet valve of the pumping chamber, adapted to intermittently pressurize the pumping chamber during a pumping cycle, the pumping cycle defining an attempted fluid delivery stroke of the pump;

a pressure sensor directly connected to the plunger and adapted to detect the pressure, between the passive inlet valve and the passive outlet valve, exerted by the plunger on the pumping chamber;

a position sensor operatively associated with the plunger to detect the position of the plunger;

a processing unit in electronic communication with the pressure sensor and position sensor; and a memory coupled to the processing unit, wherein the memory contains programming code executed by the processing unit to process pressure data from the pressure sensor and position data from the position sensor to determine a calculated actual stroke volume of the pump for the pumping cycle from a beginning of a compression stroke of the pumping cycle to a point when the passive outlet valve opens, and to modify stroke frequency to compensate for variation between the calculated stroke volume and a desired dosage rate; and wherein the passive outlet valve is operated by the pressure exerted by the plunger on the pumping chamber, and the programming code executed by the processing unit processes pressure data from the pressure sensor to identify when the passive outlet valve has opened.

2. The medical pump of claim 1, wherein the pressure sensor is the only pressure sensor included in the medical pump.

3. The medical pump of claim 1, wherein the programming code executed by the processing unit processes the pressure data and the position data to determine a calculated pressurization volume from the beginning of the compression stroke of the pumping cycle to the point when the passive outlet valve opens, and uses the calculated pressurization volume to determine the calculated stroke volume.

4. The medical pump of claim 3, wherein the programming code executed by the processing unit determines a change in pressurization volume by subtracting the calculated pressurization volume from a nominal pressurization volume, determines a change in stroke volume by multiplying the change in pressurization volume by a ratio of pumping chamber expansion under pressure at the end of the compression stroke to pumping chamber expansion under pressure at the beginning of the compression stroke of the pumping cycle, and determines the calculated stroke volume based on the change in stroke volume.

5. The medical pump of claim 4, wherein the expected nominal pressurization volume comprises multiple nominal pressurization volumes averaged together.

6. The medical pump of claim 4, wherein the programming code executed by the processing unit determines the calculated stroke volume by adding the change in stroke volume to a nominal stroke volume.

7. The medical pump of claim 3, wherein the programming code executed by the processing unit determines the calculated pressurization volume from the beginning of the compression stroke to the point when the passive outlet valve opens by converting an angle at which the passive outlet vale opens to a displacement distance of the plunger by calculating equation $x_i = L_{cam} * (1 - \cos(\theta_i))$, wherein $x_i$ is the displacement distance, $L_{cam}$ is half a distance of a stroke of the plunger, and $\theta_i$ is an angular position of the plunger at which the passive outlet valve opens, and converts the displacement distance $x_i$ into the calculated pressurization volume based on a ratio of volume to displacement distance for the pump.

8. The medical pump of claim 7, wherein the programming code executed by the processing unit determines the ratio of the volume to the displacement distance for the pump based on a nominal pressurization volume and a nominal displacement distance for a typical pump.

9. The medical pump of claim 8, wherein the nominal pressurization volume and the nominal displacement distance is provided using empirical evidence of an average normal stroke volume for all pumps of a particular type or for the particular pump.

10. The medical pump of claim 1 further comprising a cassette for defining the pumping chamber.

11. The medical pump of claim 1, wherein the pumping chamber is pressurized for a plurality of attempted fluid delivery strokes and the calculated stroke volume is an average taken over the plurality of attempted fluid delivery strokes.

12. The medical pump of claim 1, wherein the plunger is disposed against a flexible membrane of the pumping chamber between the passive inlet valve and the passive outlet valve, and the plunger is adapted to displace the flexible membrane to compress the pumping chamber and open the passive outlet valve.

13. The medical pump of claim 1, wherein the pressure sensor directly detects the pressure, between the passive inlet valve and the passive outlet valve, exerted by the plunger on the pumping chamber without using any intervening elements between the pressure sensor and the plunger.

14. The medical pump of claim 1, wherein the plunger is the only plunger used to intermittently pressurize the pumping chamber.

15. The medical pump of claim 1, wherein the pressure sensor is positioned outside of the pumping chamber in-line with and directly connected to the plunger between the pumping chamber and a shaft connected to a motor, wherein the shaft is configured to move the plunger against a flexible membrane of the pumping chamber to displace the flexible membrane and intermittently pressurize the pumping chamber during the pumping cycle.

16. The medical pump of claim 1, wherein the programming code executed by the processing unit does not modify the stroke frequency if the calculated stroke volume is not greater than a given threshold value until the calculated stroke volume exceeds the given threshold value.

17. The medical pump of claim 16, wherein the given threshold value is predetermined based on experimental data for a type of the pump or for the particular pump.

18. The medical pump of claim 1, wherein the programming code executed by the processing unit uses closed loop stroke feedback in which the stroke frequency is continually modified to adjust actual fluid delivery to compensate for variation in the stroke volume of fluid being delivered from the beginning of the compression stroke of the pumping cycle to the point when the passive outlet valve opens.

19. The medical pump of claim 1, wherein the memory contains the programming code executed by the processing unit to establish an expected nominal stroke volume associated with the attempted fluid delivery stroke of the pump, set a first stroke frequency based upon the desired dosage rate and the expected nominal stroke volume, thence, during pressurization of the pumping chamber for at least one attempted fluid delivery stroke, process the pressure data from the pressure sensor and the position data from the position sensor to determine a calculated actual stroke volume of the pump for the pumping cycle from the beginning of the compression stroke of the pumping cycle to the point when the passive outlet valve opens, and, if the calculated actual stroke volume is greater than a given threshold value, to modify the first stroke frequency to a second stroke frequency different than the first stroke frequency in order to compensate for variation between the calculated actual stroke volume and the expected nominal stroke volume so as to more closely approach the desired dosage rate during a subsequent pumping cycle.

20. The medical pump of claim 19, wherein the passive outlet valve is operated by the pressure, between the passive inlet valve and the passive outlet valve, exerted by the plunger on the pumping chamber, and the programming code executed by the processing unit processes the pressure data from the pressure sensor to identify when the passive outlet valve has opened.

21. The medical pump of claim 20, wherein the programming code executed by the processing unit uses closed loop stroke feedback in which the stroke frequency is continually modified to adjust actual fluid delivery to compensate for variation in the actual stroke volume of fluid being delivered from the beginning of the compression stroke of the pumping cycle to the point when the passive outlet valve opens.

22. A medical pump for use with a pumping chamber, comprising:
a plunger, disposed between a passive inlet valve and a passive outlet valve of the pumping chamber, adapted to intermittently pressurize the pumping chamber during a pumping cycle, the pumping cycle defining an attempted fluid delivery stroke of the pump;
a pressure sensor directly connected to the plunger and adapted to detect the pressure, between the passive inlet valve and the passive outlet valve, exerted by the plunger on the pumping chamber;
a position sensor operatively associated with the plunger to detect the position of the plunger;
a processing unit in electronic communication with the pressure sensor and position sensor; and
a memory coupled to the processing unit, wherein the memory contains programming code executed by the processing unit to establish an expected nominal stroke volume associated with the attempted fluid delivery stroke of the pump, set a first stroke frequency based upon a desired dosage rate and the expected nominal stroke volume, thence, during pressurization of the pumping chamber for at least one attempted fluid delivery stroke, process pressure data from the pressure sensor and position data from the position sensor to:
identify by a slope change in the pressure data when the passive outlet valve of the pumping chamber has opened,
determine a calculated pressurization volume from a beginning of the pumping cycle to the point when the passive outlet valve opens,
determine a change in pressurization volume by subtracting the calculated pressurization volume from a nominal pressurization volume,
determine a change in stroke volume by multiplying the change in pressurization volume by a ratio of pumping chamber expansion under pressure at the end of the compression stroke of the pumping cycle to pumping chamber expansion under pressure at the beginning of a compression stroke of the pumping cycle,
determine a calculated actual stroke volume based on the change in stroke volume, and, if the calculated actual stroke volume is greater than a given threshold value, modify the stroke frequency to a second stroke frequency that is different than the first stroke frequency in order to compensate for variation between the calculated actual stroke volume and the expected nominal stroke volume; and wherein the passive outlet valve is operated by the pressure, between the passive inlet valve and the passive outlet valve, exerted by the plunger on the pumping chamber.

23. The medical pump of claim 22 further comprising a cassette for defining the pumping chamber.

24. The medical pump of claim 22, wherein the plunger is disposed against a flexible membrane of the pumping chamber between the passive inlet valve and the passive outlet valve, and the plunger is adapted to displace the flexible membrane to compress the pumping chamber and open the passive outlet valve.

25. The medical pump of claim 22, wherein the pressure sensor directly detects the pressure, between the passive inlet valve and the passive outlet valve, exerted by the plunger on the pumping chamber without using any intervening elements between the pressure sensor and the plunger.

26. The medical pump of claim 22, wherein the plunger is the only plunger used to intermittently pressurize the pumping chamber.

27. The medical pump of claim 22, wherein the pressure sensor is positioned outside of the pumping chamber in-line with and directly connected to the plunger between the pumping chamber and a shaft connected to a motor, wherein the shaft is configured to move the plunger against a flexible membrane of the pumping chamber to displace the flexible membrane and intermittently pressurize the pumping chamber during the pumping cycle.

28. A medical pump for use with a cassette having a pumping chamber, comprising:
a plunger, disposed between a passive inlet valve and a passive outlet valve of the pumping chamber, operatively associated with a shaft and adapted to intermittently pressurize the pumping chamber during a pumping cycle, the pumping cycle defining an attempted fluid delivery stroke of the pump;
a pressure sensor positioned outside of the pumping chamber in-line with and directly connected to the plunger between the pumping chamber and the shaft connected to a motor, wherein the shaft is configured to move the plunger against a flexible membrane of the pumping chamber to displace the flexible membrane and intermittently pressurize the pumping chamber during the pumping cycle, the pressure sensor being adapted to detect the pressure, between the passive inlet valve and the passive outlet valve, exerted by the plunger on the pumping chamber;
a position sensor operatively associated with the plunger to detect the position of the plunger;
a processing unit in electronic communication with the pressure sensor and position sensor; and
a memory coupled to the processing unit, wherein the memory contains programming code executed by the processing unit to establish an expected nominal stroke volume associated with the attempted fluid delivery stroke of the pump, set a first stroke frequency based upon a desired pump flow rate and the expected nominal stroke volume, thence, during pressurization of the pumping chamber for at least one attempted fluid delivery stroke, to process pressure data from the pressure sensor and position data from the position sensor to determine a calculated actual stroke volume of the pump for the pumping cycle, and to modify the first stroke frequency to a second stroke frequency different than the first stroke frequency in order to compensate for variation between the calculated actual stroke volume and the expected nominal stroke volume so as to more closely approach the desired pump flow rate for a subsequent pumping cycle; and wherein the passive outlet valve is operated by the pressure, between the passive inlet valve and the passive outlet valve, exerted by the plunger on the pumping chamber, and the programming code executed by the processing unit processes pressure data from the pressure sensor to identify when the passive outlet valve has opened.

29. The medical pump of claim 28, wherein the flexible membrane of the pumping chamber is disposed between the passive inlet valve and the passive outlet valve, and the plunger is adapted to displace the flexible membrane to compress the pumping chamber and open the passive outlet valve.

30. The medical pump of claim 28, wherein the pressure sensor directly detects the pressure, between the passive inlet valve and the passive outlet valve, exerted by the plunger on the pumping chamber without using any intervening elements between the pressure sensor and the plunger.

31. The medical pump of claim 28, wherein the plunger is the only plunger used to intermittently pressurize the pumping chamber.

32. A medical pump for use with a pumping chamber, comprising:
   a plunger, disposed between a passive inlet valve and a passive outlet valve of the pumping chamber, adapted to intermittently pressurize the pumping chamber during a pumping cycle, the pumping cycle defining an attempted fluid delivery stroke of the pump;
   a pressure sensor positioned outside of the pumping chamber in-line with and directly connected to the plunger between the pumping chamber and a shaft connected to a motor, wherein the shaft is configured to move the plunger against a flexible membrane of the pumping chamber to displace the flexible membrane and intermittently pressurize the pumping chamber during the pumping cycle, and the pressure sensor is adapted to detect the pressure exerted by the plunger on the pumping chamber;
   a position sensor operatively associated with the plunger to detect the position of the plunger;
   a processing unit in electronic communication with the pressure sensor and position sensor; and
   a memory coupled to the processing unit, wherein the memory contains programming code executed by the processing unit to process pressure data from the pressure sensor and position data from the position sensor to determine a calculated actual stroke volume of the pump for the pumping cycle, and to modify stroke frequency to compensate for variation between the calculated stroke volume and a desired dosage rate; and
   wherein the passive outlet valve is operated by the pressure exerted by the plunger on the pumping chamber, and the programming code executed by the processing unit processes pressure data from the pressure sensor to identify when the passive outlet valve has opened.

33. The medical pump of claim 32, wherein the memory contains the programming code executed by the processing unit to establish an expected nominal stroke volume associated with the attempted fluid delivery stroke of the pump, set a first stroke frequency based upon the desired dosage rate and the expected nominal stroke volume, thence, during pressurization of the pumping chamber for at least one attempted fluid delivery stroke, process the pressure data from the pressure sensor and the position data from the position sensor to determine a calculated actual stroke volume of the pump for the pumping cycle, and, if the calculated actual stroke volume is greater than a given threshold, to modify the first stroke frequency to a second stroke frequency different than the first stroke frequency in order to compensate for variation between the calculated actual stroke volume and the expected nominal stroke volume so as to more closely approach the desired dosage rate during a subsequent pumping cycle.

34. The medical pump of claim 33, wherein the pressure sensor is adapted to detect the pressure, between the passive inlet valve and the passive outlet valve, exerted by the plunger on the pumping chamber, and the passive outlet valve is operated by the pressure, between the passive inlet valve and the passive outlet valve, exerted by the plunger on the pumping chamber.

35. A medical pump for use with a pumping chamber, comprising:
   a plunger, disposed between a passive inlet valve and a passive outlet valve of the pumping chamber, adapted to intermittently pressurize the pumping chamber during a pumping cycle, the pumping cycle defining an attempted fluid delivery stroke of the pump;
   a pressure sensor directly connected to the plunger and adapted to detect the pressure, between the passive inlet valve and the passive outlet valve, exerted by the plunger on the pumping chamber;
   a position sensor operatively associated with the plunger to detect the position of the plunger;
   a processing unit in electronic communication with the pressure sensor and position sensor; and
   a memory coupled to the processing unit, wherein the memory contains programming code executed by the processing unit to process pressure data from the pressure sensor and position data from the position sensor to determine a calculated stroke volume of the pump for the pumping cycle, and, if the calculated stroke volume is greater than a given threshold value, to modify a stroke frequency in order to compensate for variation between the calculated stroke volume and a desired dosage rate and, if the calculated stroke volume is not greater than the given threshold value, does not modify the stroke frequency until the calculated stroke volume exceeds the given threshold value; and
   wherein the passive outlet valve is operated by the pressure exerted by the plunger on the pumping chamber, and the programming code executed by the processing unit processes pressure data from the pressure sensor to identify when the passive outlet valve has opened.

36. The medical pump of claim 35, wherein the memory contains the programming code executed by the processing unit to establish an expected nominal stroke volume associated with the attempted fluid delivery stroke of the pump, set a first stroke frequency based upon the desired dosage rate and the expected nominal stroke volume, thence, during pressurization of the pumping chamber for at least one attempted fluid delivery stroke, process the pressure data from the pressure sensor and the position data from the position sensor to determine a calculated actual stroke volume of the pump for the pumping cycle, and, if the calculated actual stroke volume is greater than a given threshold value, to modify the first stroke frequency to a second stroke frequency different than the first stroke frequency in order to compensate for variation between the calculated actual stroke volume and the expected nominal stroke volume so as to more closely approach the desired dosage rate during a subsequent pumping cycle, and, if the calculated actual stroke volume is not greater than the given threshold value, does not modify the first stroke frequency until the calculated actual stroke volume exceeds the given threshold value.

37. The medical pump of claim 36, wherein the passive outlet valve is operated by the pressure, between the passive inlet valve and the passive outlet valve, exerted by the plunger on the pumping chamber.

* * * * *